United States Patent [19]

Eliachar et al.

[11] Patent Number: 5,048,518
[45] Date of Patent: Sep. 17, 1991

[54] STOMA STENT SYSTEM

[75] Inventors: Isaac Eliachar, Pepper Pike; Dat Nguyen, Lyndhurst, both of Ohio; Charles Lane, Duxbury; Lewis H. Marten, Quincy, both of Mass.

[73] Assignee: Hood Laboratories, Pembroke, Mass.

[21] Appl. No.: 460,822

[22] Filed: Jan. 4, 1990

[51] Int. Cl.$^5$ .................... A61M 16/00; A62B 9/06
[52] U.S. Cl. ..................... 128/207.14; 128/207.15; 128/207.16; 128/200.24
[58] Field of Search ............. 128/200.24, 200.26, 128/204.17, 205.27, 205.28, 205.29, 207.14, 207.15, 207.16

[56] References Cited

U.S. PATENT DOCUMENTS

| | | | |
|---|---|---|---|
| 2,039,142 | 4/1936 | Brehm | 128/207.16 |
| 2,786,469 | 3/1957 | Cohen | 128/200.26 |
| 2,804,076 | 8/1957 | Giraudon | 128/207.16 |
| 3,088,466 | 5/1963 | Nichols | 128/200.26 |
| 3,137,299 | 6/1964 | Tabor | 128/207.16 |
| 3,263,684 | 8/1966 | Bolton | 128/207.16 |
| 3,330,271 | 7/1967 | Hozier | 128/205.29 |
| 3,827,440 | 8/1974 | Birch et al. | 128/207.16 |
| 3,844,290 | 10/1974 | Birch et al. | 128/207.16 |
| 3,902,009 | 11/1975 | Olsen | 128/205.29 |
| 4,269,184 | 5/1981 | Montgomery | 128/200.26 |
| 4,325,366 | 4/1982 | Tabor | 128/207.16 |
| 4,338,930 | 7/1982 | Williams | 128/200.26 |
| 4,463,757 | 8/1984 | Schmidt | 128/205.29 |
| 4,598,705 | 7/1986 | Lichtenberger | 128/200.26 |
| 4,759,356 | 7/1988 | Muir | 128/207.16 |
| 4,763,645 | 8/1988 | Kapp | 128/205.29 |
| 4,802,474 | 2/1989 | Beevers | 128/207.14 |
| 4,809,693 | 3/1989 | Rangoni et al. | 128/207.16 |

FOREIGN PATENT DOCUMENTS 1207144 8/1959 France ..................... 128/207.14

Primary Examiner—Edgar S. Burr
Assistant Examiner—Kimberly L. Asher
Attorney, Agent, or Firm—Kane, Dalsimer, Sullivan, Kurucz, Levy, Eisele and Richard

[57] ABSTRACT

A stoma stent system for treating patients after tracheostomy and maintenance of a tracheastomy tract includes a tubular stent for insertion in the trachea and several plug components which may be inserted into the open, free end of the stent for several functions. For example, a plug may have several inserts for progressively constricting air flow through the stent to wean the patient off the stent. The same, or another plug may include a vapor source for transferring moisture from exhaled air to inhaled air. A third plug may include a check valve which blocks exhaled air and redirects the air toward the vocal cords to permit the patient to speak and cough.

18 Claims, 4 Drawing Sheets

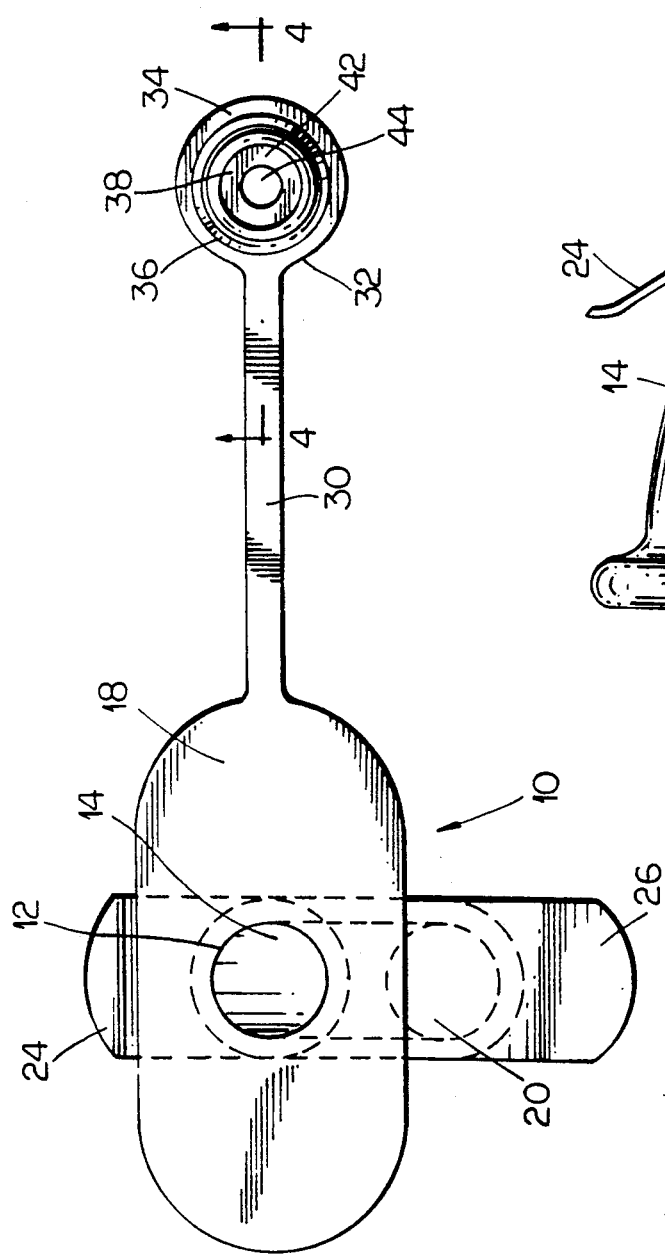
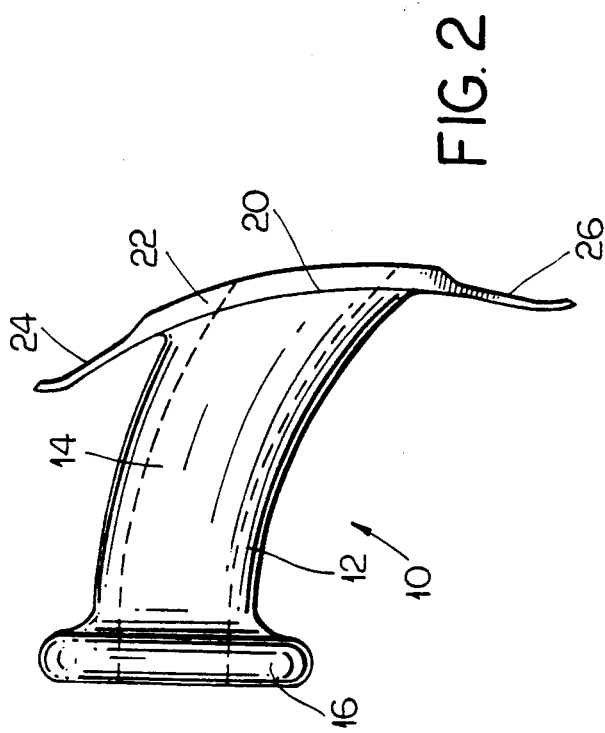

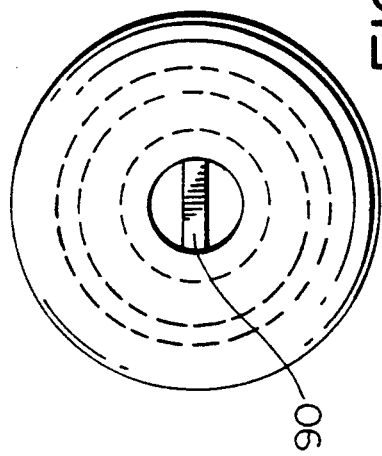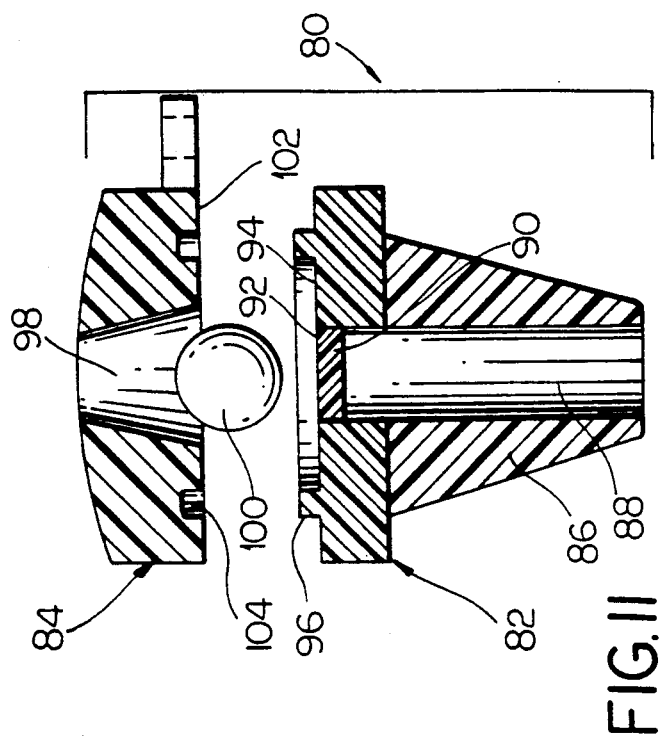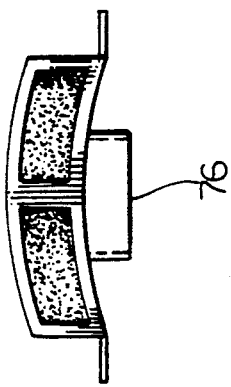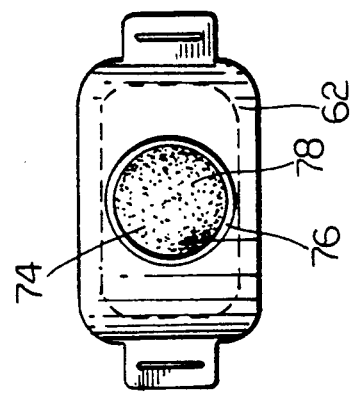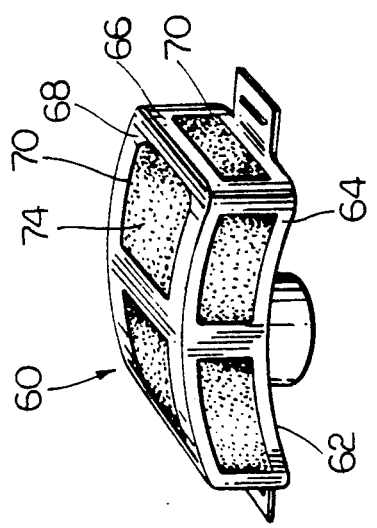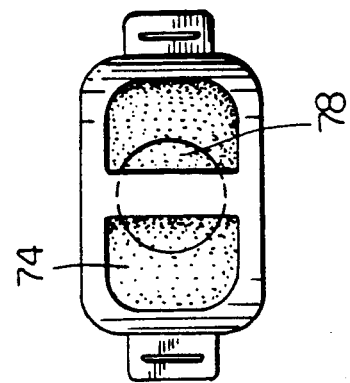

STOMA STENT SYSTEM

BACKGROUND OF THE INVENTION a. Field of Invention

This invention pertains to a tracheal device which permits a patient to breath after a tracheostomy, and more particularly a stoma stent system with modular replaceable elements for modifying and/or controlling air flow therethrough.

b. Description of the Prior Art

After a patient has undergone a tracheostomy, he is often provided with a tubular prosthesis including air channel means between the trachea and the outside ambient air. The prosthesis is held in place in the stoma so that it may be used for long time periods, maintaining patency of the tracheostomy. Such prothesis known as stoma stents are available for example from Hood Laboratories, as described in the brochure entitled QUALITY INTO LIFE, volume 1, No. 1, Spring 1989, available from Hood Laboratories, Pembroke, Mass., 02359. The stoma stent described therein consists of a tubular member with an end for anchoring the stent in a trachea and a plug tethered to the tubular member, for selectively closing the stent opposing, open end.

However, the stoma stent described above is not adaptable to certain phynolopal conditions. For example, with the tethered plug removed from the end, the tubular member is wide open, permitting phlegm and other body fluids to escape or foreign materials to be inhaled. Furthermore, dry air inhaled through the stent is uncomfortable and undesirable, drying out delicate mucous membranes.

A further physiological problem associated with prior art stents is that a patient with an open stent cannot use his vocal cords to speak. Certain embodiments of the system of the present invention provide relief for this problem.

Finally, it is known that after extended use of the stoma stent, the patient's breathing muscles atrophy so that he needs retraining to breath and speak normally. The stoma stent presently available is not useful to assist in retraining the patient.

SUMMARY OF THE INVENTION

In view of the above, an objective of the present invention is to provide a stoma stent system with various elements which may be installed for controlling or modifying air flow therethrough.

A particular objective is to provide a stoma stent with a plurality of restrictive means which may be selected to restrict air flow and thereby wean the patient from a need for the stoma stent.

Another objective is to provide a filter means which may be positioned to control the volume, humidity and temperature of the air flowing through a stoma stent.

A further objective is to provide a check valve means for restricting air flow in one direction (exhalations) to enable a patient to talk, and cough and expell aspirates.

Other objectives and advantages of the invention shall become apparent from the following description of the preferred embodiments of the invention. A stoma stent system constructed in accordance with the invention comprises of a tubular member adapted by size and configuration for use in a tracheostomy and air modifying means constructed and arranged to couple to the tubular member for modifying air flowing therethrough. The modifying means may include ring-shaped members of various diameters to gradually reduce air volume flowing through the tube, a check valve for allowing air flow for inhalation only, and/or a filter for controlling humidity within the trachea, air volume flowing through the system and particulate or liquid materials carried in the air flow.

BRIEF DESCRIPTION OF THE DRAWINGS

FIG. 1 is an end view of a stoma stent component used in accordance with this invention with an air flow modification means.

FIG. 2 shows a side view of the stoma stent of FIG. 1.

FIG. 7 shows an orthogonal view of a filter assembly for attachment to the plug in FIG. 6.

FIG. 8 shows a top view of the assembly of FIG. 7.

FIG. 9 shows a side view of the assembly of FIG. 7.

FIG. 10 shows a bottom view of the assembly of FIG. 7.

FIG. 11 shows a blown-up view of a plug for the stoma stent of FIG. 1, with a check valve.

FIG. 12 shows a top view of the plug of FIG. 11.

DETAILED DESCRIPTION OF THE INVENTION

Figure 5:
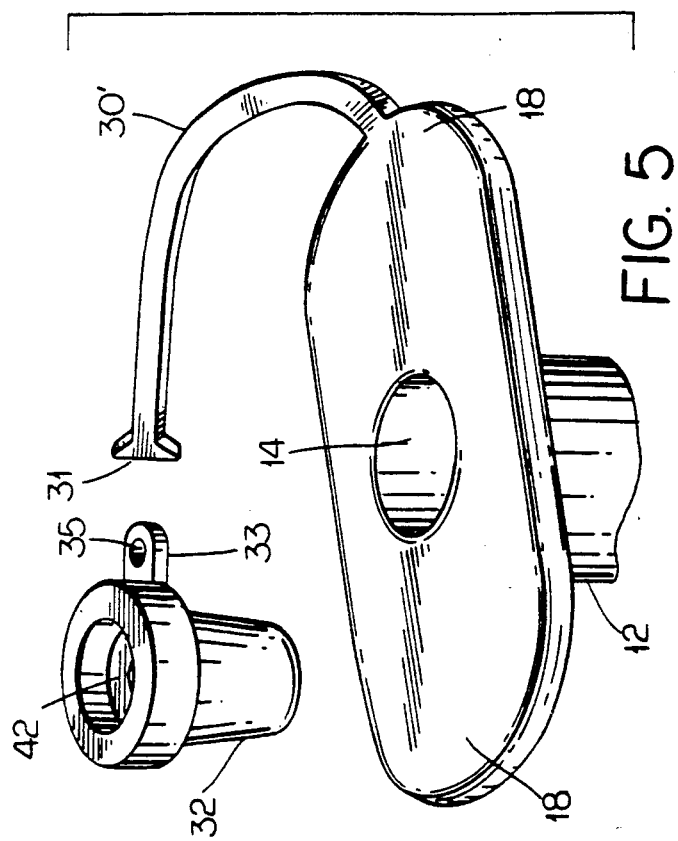
FIG. 5 shows the plug of FIG. 4 associated with a stent open end.

Referring now to FIGS. 1-13, a stoma stent system constructed in accordance with this invention will be seen. The system includes a stoma stent 10 which consists of stent tube 12 with a lumen 14. The tube 12 has a first open end 16 provided with an enlarged somewhat oval outer retention plate 18 disposed about the opening periphery. The tube 12 also has a second open end 20 provided with a second retention plate 22 with a pair of opposed flanges 24, 26. Tube 12 is curvilinear as shown best in FIG. 2, to conform to the anatomical needs of a tracheostomy incision. The retention plates 18, 22 are radially disposed about the open ends 16, 20, respectively of tube 12 and are integrally molded with the tube component 12 of stent 10. After a tracheostomy, the stent 10 may be inserted into the stomas with the plate 22 disposed through the incision into the trachea, and the plate 18 disposed outside the incision, against the patient's neck.

Figure 3:
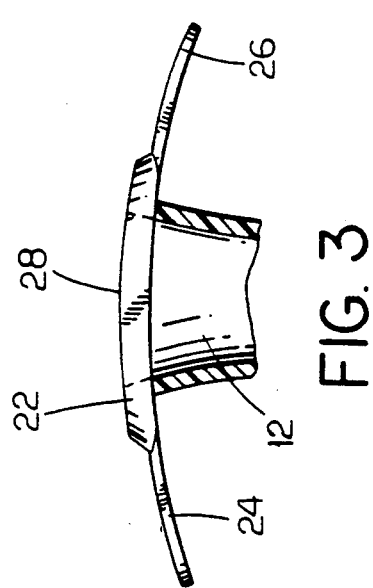
FIG. 3 shows a detailed view of a flange component used to hold the stoma stent of FIG. 1 in the trachea of a patient.

The inner retention plate 22, as shown in more detail in FIG. 3, has a relatively thick central section 28 about the periphery of open end 20 which gives firmness to the plate 22 to insure that the stent 10 stays in the trachea. The two flanges 24, 26 thin out from the central section 28 in a feathered style so that they are relatively thin and flexible. This structure insures that the plate 22 blends in with the natural tissues of the trachea to insure that the stent 10 is not rejected by adhering to the anterior wall of the trachea with a soft spring-like pressure. The vertical placement also minimizes irritation, does not initiate scar tissue growth and minimizes injury to the tissues as the tube is inserted or retracted in the incision. This feather structure also minimizes the possibility that fluids within the trachea accumulate around the plate 22 to produce infection, and /or irritation. In the FIGS. 1-3, the plate 22 is shown as curved longitudinally.

Figure 4:
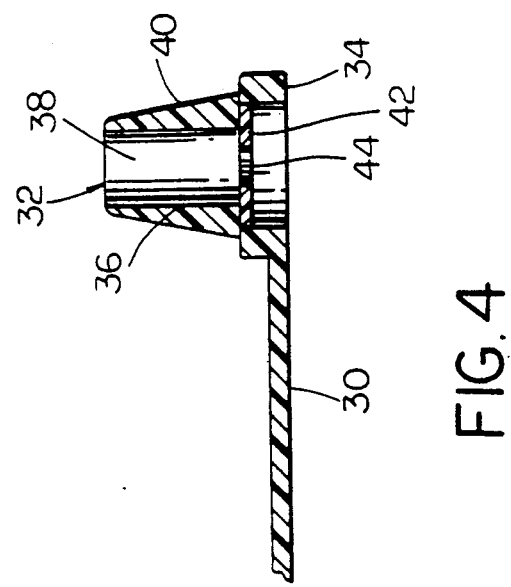
FIG. 4 shows detail in a side sectional view along line 4—4 of FIG. 1.

As shown in FIG. 1, a tether 30 is used to secure a plug 32. As seen in FIG. 4, a cross-sectional side view, along lines 4—4 of FIG. 1, the plug 32 has an annular hub 34 attached axially to cylindrical wall 36. The wall 36 has an inner through hole 38 of substantially uniform diameter, and an outer wall 40. The outer wall 40 is tapered for example at an angle of from 1° to 6°, preferably about 3°. The plug 32 is of a dimension and configuration to fit tightly into lumen 14 of tube 12, with hub 34 abutting plate 18. A preferred length of wall 40 is from about 5 to about 15 mm, which in combination with the above-described degrees of taper facilitates removal of plug 32 from the lumen of the tube 12. The outer wall 40 insures an interference fit in the lumen of tube 12 so that the plug does not fall out by itself. Inside hub 34, there is provided a toroidal or disk shaped insert 42. The insert is preferably replaceable and has a through hole 44 in open communication with to the hole 38 of wall 36. The hole 44 ma be dimensioned to have a smaller diameter than hole 38. Preferably, several inserts 42 are provided in the system of the invention, with each insert 42 having a hole 44 of different diameter. These may be selected with progressively smaller holes 44 and used to wean a patient from a need for the stoma stent. When the plug 32 is inserted into open end 14, the effective diameter of the tube 12 lumen 14 is reduced, decreasing flow of air flow. This retrains the patient to use his muscles for normal breathing. After a predetermined time period, the insert 42 is removed from hub 34 and is replaced with another insert 42 having a smaller diameter hole 44 to decrease air flow further. Thus, slowly the patient is forced to increase the use of breathing muscles and start breathing normally, without need for the tracheostomy.

In FIG. 1, plug 32 is permanently attached to plate 18 by tether 30. In a different embodiment, a tether 30' may be used which as shown in FIG. 5, may be terminated with a T-shaped end 31. For this embodiment, plug 32 (and all other plugs of the system) is provided with an ear 33 each with a through hole 35. Before the plug is installed into the open end 16, T-shaped cylinder or arrow-shaped end 31, which is flexible, is inserted into hole 35 thereby tethering plug 32 to plate 18 in a removable manner.

Figure 6:
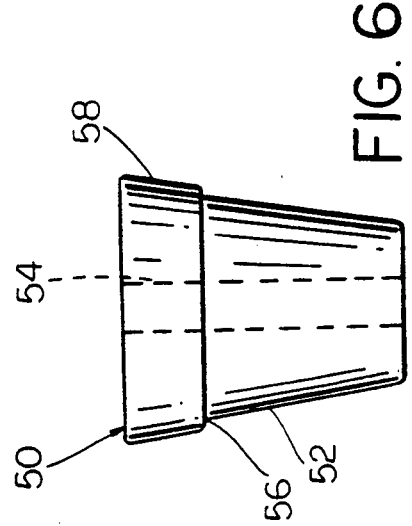
FIG. 6 shows a side view of a plug adapted for coupling with a filter means.

As the patient breathes in and out of the stoma stent 10 tube 12, the air from the ambient environment may have a relatively low humidity level. Therefore it is advantageous to provide a vapor source between the trachea and the ambient air for example in the form of a wet or wettable filter. For this purpose a plug 50 is provided as part of the stoma stent system which, as shown in FIG. 6, is generally cylindrical, with an outside configuration like that of plug 32. Thus, plug 50 may be inserted with an interference fit into the stent 10 tube 12 in a manner similar to plug 32 described above. Although for purposes of illustration, the stent system described herein includes separate plugs for selectively restricting the air flow (plug 32), and for providing a vapor source (plug 50), in fact a common plug may be used for both functions. Plug 50 is provided with an axial hole 54, and 17 also has a circumferential shoulder 56 on outer wall 52. This shoulder 56 together with an upper part 58 of the wall 52 cooperate to form a male connector for a female appliance, component of the system of the invention.

As shown in FIGS. 7-10 one vapor source means includes a filter housing 60 which is generally box-shaped with a slight curvature so that it can be worn easily on the neck under the patient's clothing. The housing 60 includes a bottom wall 62, side walls such as 64, and 66, and a top wall 68. The side walls 64, 66 and the top wall 68 each are provided with rectangular apertures which permit the installation and removal of a resilient filter material 74 disposed within the housing. Bottom wall 62 is provided with a ring shaped wall 76 surrounding a circular aperture 78. The aperture 78 and wall 76 cooperate to form a female connector for coupling to the male connector part 58 on plug 50 in FIG. 6.

The vapor source means operates as follows. The housing 60 with filter 74 is mounted on plug 50 by coupling the corresponding male-female connectors. In this manner air flowing through the lumen 14 of stent tube 12 must pass through the filter 74 and apertures 70. Moisture from exhaled air is captured and retained by the filter 74 and reused to humidify the inhaled air. Advantageously, the filter 74 is constructed from a synthetic, polymeric resin in a filament form. Representation of such filaments are filaments fabricated from polyolefins, polyamides and like resins. The air permeability of filter 74 is not critical and may be chosen so as to provide comfortable flow of air required for adequate respiration. The described arrangement has two further advantages: in cold weather the exhaled air also warms the filter thereby providing to the inhaled air not only moisture but also a source of heat. Furthermore, the filter intercepts either mucus expelled from the trachea or foreign materials from the environment, thereby protecting the environment and the patient from cross-contamination. The filter material 74 may be changed by the patient at regular intervals by snapping the housing 62 off the plug 50 and then removing the filter from the housing. If necessary, the filter may also be removed at intervals and wetted to further increase the moisture content of the inhaled air.

As mentioned above, the air-permeability of the filter 74 may be selected within very broad ranges for its function as a filtration, humidifying and warming means so long as it facilitates respiration of the patient. In general a permeability of from about 100 to about 500 cu.ft./min./ft$^2$ is advantageous. However, in another embodiment of the invention, air-permeability of the filter 74 may be selected so as to provide another means of progressively restricting the volume of air passage through the stent 10 tube 12. More specifically, by using a series of filters 74 with increasing lower air-permeability, one can restrict the volume of air passing through the stent 10 in the same manner obtained by use of inserts 42 with varied hole 44 diameters. Thus, one can use varied filter 74 air-permeances to retrain the patient's muscles for normal breathing without a tracheostomy. For this purpose, air filters having air-permeances of from about 100 to about 600 cu.ft./min./ft$^2$ may be selected for advantageous use. For example, the filter may be made of an open cell foam with up to 20% pores, or an equivalent paper filer.

The use of either inserts 42 or filters 74 and the component means of attachment to stent 10 are also useful, with a fixed air permeability or passage size for victims of the sleep apnea syndrome who have received tracheostomies as a means of managing this affliction. Often, as treatments of the sleep apnea syndrome progresses, it is advantageous to change the volume of air permitted to be exhaled through the stoma stent.

Another element of the stoma stent system is a one way check valve 80 as illustrated in the cross-sectional side view of FIG. 11. The check valve may be made of a relatively rigid plastic lightweight material in which case it has the components: a tubular member 82 and a cap 84. The tubular member 82 has a cylindrical wall 86 which is preferably tapered and has a size and configuration as described above for plug 32. The member 82 also has an axial passage 88 with a partially closed transversal member 90 having a top surface 92 substantially even with a top surface 94 of member 82. On top surface 94 there is also an annular ring 96.

Cap 84 is generally toroidal with an axial passage 98 tapered to form a seat for a valve ball 100. Cap 84 also has a bottom surface 102 facing top surface 94, and is provided with an annular groove 104 matching in shape and size to receive annular ring 96. The check valve 80 is assembled by placing the cap 84 over member 82 with the annular ring 96 disposed in groove 104, and ball 100 captured therebetween. The cap 84 may preferably then be secured to the member 82 by any well known means such as ultrasonic welding, using an adhesive or like means. Alternatively, the check valve 80 may be made unitary in a simple operation if it is made of a relatively flexible material whereby, the ball 100 is forced into the passage 98 after the main body 82-84 is formed.

The check valve 80 operates as follows. The check valve 80 is inserted into open end 14 of stent 10 tube 12 and is maintained there by an interference fit between the side walls of the tube 12 and the tapered outside wall 86 of member 82. When air is inhaled by the patient, the air flow urges the ball toward surface 92, opening passage 98. Surface 92 insures that ball 100 does not block passage 88 and allows open communication and flow of air between passage 88 and outside ambient air. When the patient exhales, ball 100 is urged against wall 98 blocking the air flow out of passage 98. Therefore, the patient is able to exhale through his normal air passages and allows him to use his vocal cords for speaking and cough to clear his throat.

Figure 13:
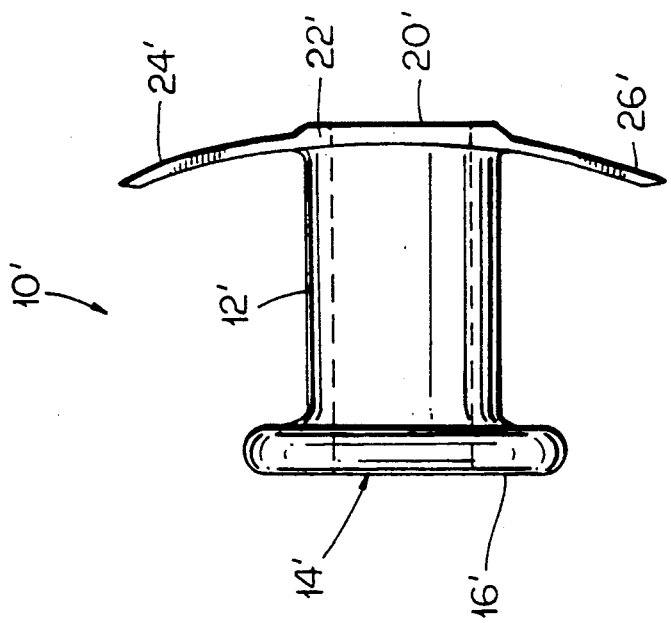
FIG. 13 shows a side view of an alternate embodiment stoma stent tube component for the stent system of this invention.

The embodiment stoma stent shown in FIGS. 1-3 shows a curved stent tube 12. However under certain circumstances, for instance recently created tracheostomies, a system with a straight tube 12' as shown in FIG. 13 may be used to advantage. The stoma stent 10' shown in FIG. 13 (side view) is in all other respects identical to stent 10, and like parts are shown with the same numeral designations, with an added prime mark. The stent 10 and auxiliary components may be fabricated from any conventional material, the preferred stent 10 of is advantageously molded from a medical grade (Food and Drug Administration approved) of yielding plastic stock material such as a silicone rubber, by known and conventional molding techniques. A silicone rubber is herein defined generally as a cross-linked silicone elastomer of the type vulcanized at room temperature (RTV) or at elevated temperature (HTV). Dimethyl siloxanediol with silicone resin or alkyl silicate as cross-linking agents are typically used. Typically, fillers such as silica, calcium carbonate, titanium oxide and the like are normally added to the polymer formulation, usually by the manufacturer of the silicone polymer, as the filler materials provide degrees of rigidity and softness.

One example of a silicone rubber which may be used in the cannulas and the stents of the invention is Dow Corning 3110 RTV silicone rubber. This material can be cross-linked at room temperature with Dow Corning RTV catalyst No. 4. Other silicone rubber resins are well known and available commercially and techniques of molding them are well know to the artisan. The plugs 32, 50 and 80 described above may be made from the same, or a different material then the stent 10.

Obviously numerous modifications may be made to the embodiments of the invention described above without departing form its scope as defined in the appended claims.

The stoma stent system of the invention may be constructed in any desired size, adapted to treat adults, children, infants of any age. Furthermore, it is apparent that the structure described and claimed herein is advantageous because it does not encroach on the inner trachael lumen, it is easy to insert and remove and it eliminates the detrimental effects of a standard cannula. In addition, the device prevents buckling of the anterior tracheal wall.

What is claimed is:

1. A stoma stent system for the treatment of a patient after a tracheostomy comprising:
    an elongated open tube for disposition in an incision made between the trachea of a patient and the environment to provide a path for an air flow; and
    means for weaning a patient off of said stoma stent comprising modifying means for selectively modifying said air flow by selectively changing the air flow resistance in said tube
    said tube having a tube diameter and said modifying means including a plurality of replaceable air restricting members, each member having a hole of a different size with a restriction diameter smaller than said tube diameter, said air flow resistance being modified by placing one of said replaceable air restricting members into said tube, wherein all the air flow passing from the tube passes through said hole.

2. The stoma stent system of claim 1 wherein said modifying means includes value means for blocking the air flow in a preselected direction.

3. The stoma stent system of claim 1 wherein said modifying means includes filter means for filtering said air flow.

4. The stoma stent system of claim 3 wherein said filter means comprises a plurality of replaceable filter, each filter having a different air resistance, with one of said filters being placed inside said tube for restricting air flow therethrough.

5. The stoma stent system of claim 1 wherein said modifying means includes a vapor source.

6. An assembly for treating a person having a tracheostomy incision, said assembly comprising:
    A. a stoma stent including a tube adapted by size and configuration to be inserted into a tracheal incision, said tube having an open end for providing a path for an air flow; and
    B. means for weaning a person off the stoma stent, said weaning means comprising a plurality of air restricting members mountable on said open end, said air restricting members selectively restricting said path, each said air restricting member having a different air resistance whereby a person can be weaned from said stoma stent by changing sequentially said air restricting members to gradually increase air resistance through said path.

7. The assembly of claim 6 wherein the tube has a tube diameter and said air restricting members each have a restriction hole with a diameter smaller than said tube diameter.

8. The assembly of claim 6 wherein said modifying means includes valve means for blocking the air flow in a preselected direction.

9. The assembly of claim 6 wherein said air restricting members each include a filter for filtering said air flow each said filter having a different air flow resistance.

10. The assembly of claim 6 wherein said air restricting members include a vapor source.

11. The assembly of claim 6 further comprising plug means fitting in said open end, said plug means including means for selectively accepting one of said air restricting members.

12. The assembly of claim 11 wherein said plug means is removably attached to said tube.

13. The assembly of claim 12 further comprising tethering means for integrally coupling said plug means to said tube.

14. A stoma stent system comprising:
a tube having a first end, and a second end wherein said first end is open to the atmosphere when said tube is inserted into a person's trachea;
a cap having coupling means arranged and constructed to form an interference fit with said first end when said cap is mounted on said tube; and
means for weaning a person off said stoma stent system, said means for weaning comprising a plurality of air flow restricting members, each member having a different air flow resistance, each member being constructed to cooperate with said tube when mounted thereon to restrict air flow through said tube.

15. The system of claim 14 wherein said tube has an interior, said cap includes a cap opening in communication with said interior for providing an air path to the outside, and said air flow restricting members comprise a plurality of disks constructed and arranged for mounting in said cap opening, each said disk having a different restriction hole.

16. The system of claim 14 further comprising tethering means for tethering said cap to said tube.

17. The system of claim 14 further comprising a housing mounted on said cap, and wherein said plurality of restricting members comprise air filters, each filter being mountable in said housing one at a time, said filters having different air resistance.

18. The system of claim 14 wherein one of said air flow restricting members is a check valve.

* * * * *